(12) United States Patent
Singhal et al.

(10) Patent No.: US 8,397,732 B2
(45) Date of Patent: Mar. 19, 2013

(54) IMPLANTATION OF LOW-PROFILE IMPLANTABLE MEDICAL DEVICE

(75) Inventors: Ruchika Singhal, Minneapolis, MN (US); Robert M. Skime, Coon Rapids, MN (US); Carl D. Wahlstrand, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 795 days.

(21) Appl. No.: 10/731,868

(22) Filed: Dec. 9, 2003

(65) Prior Publication Data
US 2004/0173221 A1 Sep. 9, 2004

Related U.S. Application Data

(60) Provisional application No. 60/431,854, filed on Dec. 9, 2002, provisional application No. 60/471,262, filed on May 16, 2003, provisional application No. 60/503,945, filed on Sep. 20, 2003, provisional application No. 60/503,946, filed on Sep. 20, 2003, provisional application No. 60/507,857, filed on Oct. 1, 2003.

(51) Int. Cl.
*A61B 19/00* (2006.01)
(52) U.S. Cl. .......................................... 128/898
(58) Field of Classification Search ............... 623/11, 623/15.11, 24; 607/36, 45, 116
See application file for complete search history.

(56) References Cited

U.S. PATENT DOCUMENTS

| | | |
|---|---|---|
| 3,522,811 A | 8/1970 | Schwartz et al. |
| 3,690,325 A | 9/1972 | Kenny |
| 3,720,874 A | 3/1973 | Gorcik et al. |
| 3,724,467 A | 4/1973 | Avery et al. |
| 3,888,260 A | 6/1975 | Fischell |
| 3,913,587 A | 10/1975 | Newash |
| 3,941,135 A | 3/1976 | von Sturm et al. |
| 4,006,748 A | 2/1977 | Schulman |
| 4,010,760 A | 3/1977 | Kraska et al. |
| 4,013,081 A | 3/1977 | Kolenik |
| 4,040,412 A | 8/1977 | Sato |
| 4,094,321 A | 6/1978 | Muto |
| 4,256,115 A | 3/1981 | Bilitch |
| 4,266,552 A | 5/1981 | Dutcher et al. |
| 4,328,813 A | 5/1982 | Ray |
| 4,399,819 A | 8/1983 | Cowdery |
| 4,399,820 A | 8/1983 | Wirtzfeld et al. |
| 4,408,607 A | 10/1983 | Maurer |

(Continued)

FOREIGN PATENT DOCUMENTS

| | | |
|---|---|---|
| DE | 3940632 | 12/1990 |
| EP | 1 145 735 A2 | 10/2001 |

(Continued)

OTHER PUBLICATIONS

U.S. Appl. No. 10/837,319, filed Apr. 30, 2004, entitled "Implantable Medical Device With Anti-Infection Agent."

(Continued)

*Primary Examiner* — William H. Matthews
(74) *Attorney, Agent, or Firm* — John W. Albrecht; Shumaker & Sieffert, PA

(57) ABSTRACT

In general, the invention is directed to techniques for implantation of a low-profile implantable medical device (IMD) in the body of a patient. In an exemplary embodiment, the low-profile IMD is implanted under the scalp. When the treatment or monitoring site is in or on the head of the patient, the low-profile IMD can be implanted under the scalp proximate to the treatment or monitoring site. In one embodiment, the invention is directed to a method that includes making an incision in the scalp of a head of a patient to create a scalp flap, exposing a skull beneath the scalp flap, creating a pocket between the scalp and the skull, and placing at least a portion of a low-profile IMD in the pocket. The low-profile IMD may include a plurality of modules, covered in part by a flexible overmold.

25 Claims, 9 Drawing Sheets

U.S. PATENT DOCUMENTS

| | | |
|---|---|---|
| 4,499,907 A | 2/1985 | Kallok et al. |
| 4,503,860 A | 3/1985 | Sams et al. |
| 4,574,780 A | 3/1986 | Manders |
| 4,616,655 A | 10/1986 | Weinberg et al. |
| 4,911,178 A | 3/1990 | Neal |
| 4,928,696 A | 5/1990 | Henderson et al. |
| 4,934,368 A | 6/1990 | Lynch |
| 4,969,899 A | 11/1990 | Cox, Jr. |
| 4,972,846 A | 11/1990 | Owens et al. |
| 5,085,644 A | 2/1992 | Watson et al. |
| 5,116,345 A | 5/1992 | Jewell et al. |
| 5,144,946 A | 9/1992 | Weinberg et al. |
| 5,197,332 A | 3/1993 | Shennib |
| 5,207,218 A | 5/1993 | Carpentier et al. |
| 5,218,959 A | 6/1993 | Fenster |
| 5,220,929 A | 6/1993 | Marquit |
| 5,252,090 A | 10/1993 | Giurtino et al. |
| 5,271,397 A | 12/1993 | Seligman et al. |
| 5,312,440 A | 5/1994 | Hirschberg et al. |
| 5,314,451 A | 5/1994 | Mulier |
| 5,314,453 A | 5/1994 | Jeutter |
| 5,396,813 A | 3/1995 | Takeuchi et al. |
| H1465 H | 7/1995 | Stokes |
| 5,431,695 A | 7/1995 | Wiklund et al. |
| 5,433,734 A | 7/1995 | Stokes et al. |
| 5,455,999 A | 10/1995 | Owens et al. |
| 5,456,698 A | 10/1995 | Byland et al. |
| 5,458,997 A | 10/1995 | Crespi et al. |
| 5,477,855 A | 12/1995 | Schindler et al. |
| 5,480,416 A | 1/1996 | Garcia et al. |
| 5,489,225 A | 2/1996 | Julian |
| 5,554,194 A | 9/1996 | Sanders |
| 5,562,715 A | 10/1996 | Czura et al. |
| 5,571,148 A | 11/1996 | Loeb et al. |
| 5,613,935 A | 3/1997 | Jarvik |
| 5,638,832 A | 6/1997 | Singer et al. |
| 5,645,586 A | 7/1997 | Meltzer |
| 5,674,260 A | 10/1997 | Weinberg |
| 5,678,559 A | 10/1997 | Drakulic |
| 5,702,430 A | 12/1997 | Slimon et al. |
| 5,741,313 A | 4/1998 | Nason et al. |
| 5,748,767 A | 5/1998 | Raab |
| 5,755,743 A | 5/1998 | Volz et al. |
| 5,769,874 A | 6/1998 | Dahlberg |
| 5,776,169 A | 7/1998 | Schroeppel |
| 5,800,535 A | 9/1998 | Howard, III |
| 5,814,095 A | 9/1998 | Müller et al. |
| 5,843,150 A | 12/1998 | Adams et al. |
| 5,873,899 A | 2/1999 | Stutz, Jr. et al. |
| 5,876,424 A | 3/1999 | O'Phelan et al. |
| 5,895,414 A | 4/1999 | Sanchez-Zambrano |
| 5,896,647 A | 4/1999 | Shkuratoff |
| 5,919,215 A | 7/1999 | Haeg et al. |
| 5,935,154 A | 8/1999 | Westlund |
| 5,938,689 A | 8/1999 | Fischell et al. |
| 5,941,905 A | 8/1999 | Single |
| 5,941,906 A | 8/1999 | Barreras, Sr. et al. |
| 5,954,751 A | 9/1999 | Chen et al. |
| 5,954,757 A | 9/1999 | Gray |
| 5,958,088 A | 9/1999 | Vu et al. |
| 5,984,859 A | 11/1999 | Lesinski |
| 5,991,664 A | 11/1999 | Seligman |
| 6,006,124 A | 12/1999 | Fischell et al. |
| 6,016,449 A | 1/2000 | Fischell et al. |
| 6,016,593 A | 1/2000 | Kyrstein |
| 6,044,304 A | 3/2000 | Baudino |
| 6,061,593 A | 5/2000 | Fischell et al. |
| 6,067,474 A | 5/2000 | Schulman et al. |
| 6,091,979 A | 7/2000 | Madsen |
| 6,106,464 A | 8/2000 | Bass et al. |
| 6,112,120 A | 8/2000 | Correas |
| 6,128,538 A | 10/2000 | Fischell et al. |
| 6,131,581 A | 10/2000 | Leysieffer et al. |
| 6,134,474 A | 10/2000 | Fischell et al. |
| 6,146,390 A | 11/2000 | Heilbrun et al. |
| 6,162,487 A | 12/2000 | Darouiche |
| 6,168,580 B1 | 1/2001 | Yardley |
| 6,176,879 B1 | 1/2001 | Reischl et al. |
| 6,205,358 B1 | 3/2001 | Haeg et al. |
| 6,214,032 B1 | 4/2001 | Loeb et al. |
| 6,218,016 B1 | 4/2001 | Tedeschi et al. |
| 6,230,049 B1 | 5/2001 | Fischell et al. |
| 6,233,488 B1 | 5/2001 | Hess |
| 6,248,080 B1 | 6/2001 | Miesel et al. |
| 6,259,951 B1 | 7/2001 | Kuzma et al. |
| 6,263,225 B1 | 7/2001 | Howard, III |
| 6,266,556 B1 | 7/2001 | Ives et al. |
| 6,269,266 B1 | 7/2001 | Leysieffer |
| 6,272,382 B1 | 8/2001 | Faltys et al. |
| 6,283,997 B1 | 9/2001 | Garg et al. |
| 6,308,101 B1 | 10/2001 | Faltys et al. |
| 6,324,428 B1 | 11/2001 | Weinberg et al. |
| 6,324,433 B1 | 11/2001 | Errico |
| 6,330,468 B1 | 12/2001 | Scharf |
| 6,354,299 B1 | 3/2002 | Fischell et al. |
| 6,356,792 B1 | 3/2002 | Zonenshayn et al. |
| 6,358,281 B1 | 3/2002 | Berrang et al. |
| 6,360,122 B1 | 3/2002 | Fischell et al. |
| 6,366,813 B1 | 4/2002 | DiLorenzo |
| 6,405,079 B1 | 6/2002 | Ansarinia |
| 6,415,184 B1 | 7/2002 | Ishikawa et al. |
| 6,427,086 B1 | 7/2002 | Fischell et al. |
| 6,436,422 B1 | 8/2002 | Trogolo et al. |
| 6,445,956 B1 | 9/2002 | Laird et al. |
| 6,456,256 B1 | 9/2002 | Amundson et al. |
| 6,456,886 B1 | 9/2002 | Howard, III et al. |
| 6,480,743 B1 | 11/2002 | Kirkpatrick et al. |
| 6,490,486 B1 | 12/2002 | Bradley |
| 6,498,951 B1 | 12/2002 | Larson et al. |
| 6,516,227 B1 | 2/2003 | Meadows et al. |
| 6,517,476 B1 | 2/2003 | Bedoya et al. |
| 6,537,200 B2 | 3/2003 | Leysieffer et al. |
| 6,554,762 B2 | 4/2003 | Leysieffer |
| 6,560,486 B1 | 5/2003 | Osorio et al. |
| 6,565,503 B2 | 5/2003 | Leysieffer et al. |
| 6,567,703 B1 | 5/2003 | Thompson et al. |
| 6,575,894 B2 | 6/2003 | Leysieffer et al. |
| 6,597,954 B1 | 7/2003 | Pless et al. |
| 6,618,623 B1 | 9/2003 | Pless et al. |
| 6,626,680 B2 | 9/2003 | Ciurzynski et al. |
| 6,648,914 B2 | 11/2003 | Berrang et al. |
| 6,671,544 B2 | 12/2003 | Baudino |
| 6,726,678 B1 | 4/2004 | Nelson et al. |
| 6,782,292 B2 | 8/2004 | Whitehurst |
| 6,788,974 B2 | 9/2004 | Bardy et al. |
| 6,805,998 B2 | 10/2004 | Jenson et al. |
| 6,850,802 B2 | 2/2005 | Holsheimer |
| 6,882,881 B1 | 4/2005 | Lesser et al. |
| 6,899,976 B2 | 5/2005 | Larson et al. |
| 6,963,780 B2 | 11/2005 | Ruben et al. |
| 6,975,906 B2 | 12/2005 | Rusin et al. |
| 6,994,933 B1 | 2/2006 | Bates |
| 7,010,351 B2 | 3/2006 | Firlik et al. |
| 7,033,326 B1 | 4/2006 | Pianca et al. |
| 7,103,415 B2 | 9/2006 | Probst et al. |
| 7,107,097 B2 | 9/2006 | Stern et al. |
| 7,110,819 B1 | 9/2006 | O'Hara |
| 7,167,760 B2 | 1/2007 | Dawant et al. |
| 7,212,864 B2 | 5/2007 | Wahlstrand et al. |
| 7,242,982 B2 | 7/2007 | Singhal et al. |
| 7,263,401 B2 | 8/2007 | Scott et al. |
| 7,454,251 B2 | 11/2008 | Rezai et al. |
| 7,596,399 B2 | 9/2009 | Singhal et al. |
| 7,702,380 B1 | 4/2010 | Dean |
| 8,095,200 B2 | 1/2012 | Quaid, III |
| 2001/0033953 A1 | 10/2001 | Takeuchi et al. |
| 2001/0051819 A1 | 12/2001 | Fischell et al. |
| 2002/0002390 A1 | 1/2002 | Fischell et al. |
| 2002/0013612 A1 | 1/2002 | Whitehurst |
| 2002/0019669 A1 | 2/2002 | Berrang et al. |
| 2002/0042630 A1 | 4/2002 | Bardy et al. |
| 2002/0042634 A1 | 4/2002 | Bardy et al. |
| 2002/0051550 A1 | 5/2002 | Leysieffer |
| 2002/0059049 A1 | 5/2002 | Bradbury et al. |
| 2002/0068958 A1 | 6/2002 | Bardy et al. |
| 2002/0072770 A1 | 6/2002 | Pless |
| 2002/0077670 A1 | 6/2002 | Archer et al. |

| | | | |
|---|---|---|---|
| 2002/0087201 A1 | 7/2002 | Firlik et al. | |
| 2002/0099412 A1 | 7/2002 | Fischell et al. | |
| 2002/0103510 A1 | 8/2002 | Bardy et al. | |
| 2002/0107546 A1 | 8/2002 | Ostroff et al. | |
| 2002/0147498 A1 | 10/2002 | Tallarida et al. | |
| 2002/0161403 A1 | 10/2002 | Meadows et al. | |
| 2002/0165588 A1 | 11/2002 | Fraley et al. | |
| 2002/0169485 A1 | 11/2002 | Pless et al. | |
| 2002/0177882 A1 | 11/2002 | DiLorenzo | |
| 2003/0004428 A1 | 1/2003 | Pless et al. | |
| 2003/0004546 A1 | 1/2003 | Casey | |
| 2003/0017372 A1 | 1/2003 | Probst et al. | |
| 2003/0040781 A1 | 2/2003 | Sunderland et al. | |
| 2003/0073972 A1 | 4/2003 | Rosenman et al. | |
| 2003/0085684 A1 | 5/2003 | Tsukamoto et al. | |
| 2003/0088294 A1 | 5/2003 | Gesotti | |
| 2003/0091893 A1 | 5/2003 | Kishiyama et al. | |
| 2003/0109903 A1 | 6/2003 | Berrang et al. | |
| 2003/0120320 A1 | 6/2003 | Solom | |
| 2003/0125786 A1 | 7/2003 | Gliner et al. | |
| 2003/0130706 A1 | 7/2003 | Sheffield et al. | |
| 2003/0171787 A1 | 9/2003 | Money et al. | |
| 2003/0204229 A1 | 10/2003 | Stokes | |
| 2003/0228042 A1 | 12/2003 | Sinha | |
| 2004/0015070 A1 | 1/2004 | Liang et al. | |
| 2004/0030245 A1 | 2/2004 | Noble et al. | |
| 2004/0082977 A1 | 4/2004 | Engmark et al. | |
| 2004/0102828 A1 | 5/2004 | Lowry et al. | |
| 2004/0172090 A1 | 9/2004 | Janzig et al. | |
| 2004/0176815 A1 | 9/2004 | Janzig et al. | |
| 2004/0181263 A1 | 9/2004 | Balzer et al. | |
| 2004/0186528 A1 | 9/2004 | Ries et al. | |
| 2004/0243481 A1 | 12/2004 | Bradbury et al. | |
| 2005/0004620 A1 | 1/2005 | Singhal et al. | |
| 2005/0033378 A1 | 2/2005 | Sheffield et al. | |
| 2005/0070781 A1 | 3/2005 | Dawant et al. | |
| 2005/0070971 A1 | 3/2005 | Fowler et al. | |
| 2005/0075679 A1 | 4/2005 | Gliner et al. | |
| 2005/0159792 A1 | 7/2005 | Ridder | |
| 2005/0228249 A1 | 10/2005 | Boling | |
| 2006/0004422 A1 | 1/2006 | De Ridder | |
| 2006/0094951 A1 | 5/2006 | Dean et al. | |
| 2006/0116743 A1 | 6/2006 | Gibson et al. | |
| 2006/0129205 A1 | 6/2006 | Boveja et al. | |
| 2006/0149336 A1 | 7/2006 | Meadows | |
| 2009/0299164 A1 | 12/2009 | Singhal et al. | |
| 2009/0299165 A1 | 12/2009 | Singhal et al. | |
| 2009/0299380 A1 | 12/2009 | Singhal et al. | |

FOREIGN PATENT DOCUMENTS

| | | |
|---|---|---|
| EP | 1 145 736 A2 | 10/2001 |
| GB | 1 161 579 | 8/1969 |
| WO | WO 92/20402 | 11/1992 |
| WO | WO 00/13743 | 3/2000 |
| WO | WO 00/40295 | 7/2000 |
| WO | WO 01/10369 | 2/2001 |
| WO | WO 01/28622 | 4/2001 |
| WO | WO 01/39830 | 6/2001 |
| WO | WO 01/41858 | 6/2001 |
| WO | WO 01/60450 | 8/2001 |
| WO | WO 01/97906 | 12/2001 |
| WO | WO 02/05590 | 1/2002 |
| WO | WO 02/056637 | 7/2002 |
| WO | WO 03/026739 | 4/2003 |
| WO | WO 03/076012 | 9/2003 |
| WO | WO 2004/043536 | 5/2004 |
| WO | 2004/052459 A1 | 6/2004 |
| WO | WO 2004/052458 | 6/2004 |

OTHER PUBLICATIONS

U.S. Appl. No. 10/835,527, filed Apr. 29, 2004, entitled "Implantation of Implantable Medical Device".
U.S. Appl. No. 10/835,232, filed Apr. 29, 2004, entitled "Explanation of Implantable Medical Device."
U.S. Appl. No. 10/835,233, filed Apr. 29, 2004, entitled "Implantable Medical Device With a Nonhermetic Battery."
U.S. Appl. No. 10/835,548, filed Apr. 29, 2004, entitled "Headset Recharger for Cranially Implantable Medical Devices."
U.S. Appl. No. 10/835,245, filed Apr. 29, 2004, entitled "Battery Housing Configuration."
U.S. Appl. No. 10/837,276, filed Apr. 30, 2004, entitled "Implantable Medical Device With Lubricious Material."
U.S. Appl. No. 10/731,699, filed Dec. 9, 2003, entitled "Coupling Module of a Modular Implantable Medical Device."
U.S. Appl. No. 10/730,873, filed Dec. 9, 2003, entitled "Overmold for a Modular Implantable Medical Device."
U.S. Appl. No. 10/731,881, filed Dec. 9, 2003, entitled "Reducing Relative Intermodule Motion in a Modular Implantable Medical Device."
U.S. Appl. No. 10/730,878, filed Dec. 9, 2003, entitled "Lead Interconnect Module of a Modular Implantable Medical Device."
U.S. Appl. No. 10/730,877, filed Dec. 9, 2003, entitled "Low-Profile Implantable Medical Device."
U.S. Appl. No. 10/731,867, filed Dec. 9, 2003, entitled "Concavity of an Implantable Medical Device."
U.S. Appl. No. 10/731,638, filed Dec. 9, 2003, entitled "Modular Implantable Medical Device."
U.S. Appl. No. 10/731,869, filed Dec. 9, 2003, entitled "Modular Implantable Medical Device."
"Surgical Process," Animation Screenshots from http://www.cochlearamerica.com/800.asp, 7 pgs.
"Candidates Brochure," http://www.cochlearamerica.com/pdfs/candidatebrochglobal.pdf, 14 pgs.
"Research and Development," http://www.cochlearamericas.com/384.asp, 1 pg.
"The World Leader in cochlear implants—revolutionizing hearing for adults and infants," http://www.cochlear.com, 1 pg.
"Cochlear: innovator of the Nucleus 3 cochlear implant system," http://www.cochlearamericas.com, 1 pg.
"What is a Cochlear Implant," http://www.cochlearamericas.com/What/161.asp, 1 pg.
"ESPrit 3G Speech Processor," http://www.cochlearamericas.com/591.asp, 2 pgs.
"Nucleus 3 System," http://www.cochlearamericas.com/Products/465.asp, 1 pg.
"Internal Components: Nucleus 24 Cochlear Implants," http://www.cochlearamericas.com/374.asp, 1 pg.
"Nucleus 24 Contour," http://www.cochlearamericas.com/568.asp, 2 pgs.
"Nucleus 24 M," http://www.cochlearamericas.com/372.asp, 1 pg.
"Nucleus 24 K," http://www.cochlearamericas.com/371.asp, 1 pg.
"Nucleus 24 Double Array," http://www.cochlearamericas.com/370.asp, 1 pg.
"Nucleus 24 ABI: Auditory Brainstem Implant," http://www.cochlearamericas.com/373.asp, 2 pgs.
"Nucleus Speech Processors," http://www.cochlearamericas.com/629.asp, 1 pg.
"Sprint: body worn speech processor," http://www.cochlearamericas.com/1010.asp, 1 pg.
"Cochlear," http://www.cochlearamericas.com/Recipients/978.asp, 3 pgs.
Answers.com, www.answers.com, defined: discrete components, accessed on Mar. 2, 2007 (2 pages).

IMPLANTATION OF LOW-PROFILE IMPLANTABLE MEDICAL DEVICE

This application claims the benefit of:
1. U.S. Provisional Application entitled "CRANIAL NEUROSTIMULATOR AND METHOD," Ser. No. 60/431,854, filed on Dec. 9, 2002;
2. U.S. Provisional Application entitled "Implantable Cranial Medical Devices and Methods," Ser. No. 60/471,262, filed on May 16, 2003;
3. U.S. Provisional Application entitled "IMPLANTABLE CRANIAL MEDICAL DEVICES AND METHODS," Ser. No. 60/503,945, filed on Sep. 20, 2003;
4. U.S. Provisional Application entitled "IMPLANTABLE CRANIAL MEDICAL DEVICES AND METHODS," Ser. No. 60/503,946, filed on Sep. 20, 2003; and
5. U.S. Provisional Application entitled "Thin Neuro Stimulation System, Device and Method," Ser. No. 60/507,857, filed on Oct. 1, 2003. The entire content of each of these U.S. Provisional Applications is incorporated herein by reference.

The following co-pending and commonly-assigned U.S. patent applications, filed on even date herewith, are also incorporated herein by reference in their entirety:
1. U.S. patent application entitled "MODULAR IMPLANTABLE MEDICAL DEVICE," to Carl D. Wahlstrand et al., filed Dec. 9, 2003, Ser. No. 10/731,869;
2. U.S. patent application entitled "COUPLING MODULE OF A MODULAR IMPLANTABLE MEDICAL DEVICE," to Darren A. Janzig et al., filed Dec. 9, 2003, Ser. No. 10/731,699;
3. U.S. patent application entitled "OVERMOLD FOR A MODULAR IMPLANTABLE MEDICAL DEVICE," to Ruchika Singhal et al., filed Dec. 9, 2003, Ser. No. 10/730,873;
4. U.S. patent application entitled "REDUCING RELATIVE INTER-MODULE MOTION IN A DISTRIBUTED MODULAR IMPLANTABLE MEDICAL DEVICE," to Carl D. Wahlstrand et al., filed Dec. 9, 2003, Ser. No. 10/731,881;
5. U.S. patent application entitled "LEAD CONNECTION MODULE OF A MODULAR IMPLANTABLE MEDICAL DEVICE," to Ruchika Singhal et al., filed Dec. 9, 2003, Ser. No. 10/730,878;
6. U.S. patent application entitled "LOW-PROFILE IMPLANTABLE MEDICAL DEVICE," to Darren A. Janzig et al., filed Dec. 9, 2003, Ser. No. 10/730,877; and
7. U.S. patent application entitled "CONCAVITY OF AN IMPLANTABLE MEDICAL DEVICE," to Carl D. Wahlstrand et al., filed Dec. 9, 2003, Ser. No. 10/731,867.
8. U.S. patent application entitled "MODULAR IMPLANTABLE MEDICAL DEVICE," to Carl D. Wahlstrand et al., filed Dec. 9, 2003, Ser. No. 10/731,638

TECHNICAL FIELD

The invention relates to implantation of medical devices. The invention relates to medical devices, and more particularly, to implantable medical devices that deliver therapy to and/or monitor a patient.

BACKGROUND

Implantable medical devices (IMDs) include devices implantable in a mammalian body that sense medical parameters, monitor medical conditions, administer therapy, or any combination thereof. Typical IMDs include a variety of electrical and/or mechanical components, often including a housing that houses the components. Because the components may be fragile, the housing is usually sufficiently robust to protect the components from forces to which they would otherwise be exposed when implanted within the body. Housings may be constructed from titanium, for example. In order to avoid potentially harmful interactions between the components and bodily fluids, such as corrosion, IMD housings are typically hermetically sealed.

Large components common to most IMDs include a battery, a recharge module or coil, and a hybrid circuit that includes digital circuits, e.g., integrated circuit chips and/or a microprocessor, and analog circuit components. The components, the housing and seal elements each add bulk to the IMD.

In the case of a device having elements that interact with the head, implantation of a bulky IMD presents practical difficulties. In many cases, practical considerations weigh strongly against implantation of a bulky IMD under the scalp and on top of the cranium, and the IMD may have to be implanted at a site remote from the scalp. A typical case involves a sensor or stimulator having leads implanted in the brain. Implantation of the IMD requires several distinct invasive stages, often requiring multiple surgical operations.

For example, implantation of a neurostimulator can include several stages. A first stage entails placement of the leads that deliver stimulation to the brain. The surgeon incises the scalp of the patient and draws the scalp away from the skull. The physician then deploys the leads through burr holes in the skull. In a second state, the physician creates a second incision, such as an incision behind an ear. The surgeon tunnels the leads to the second incision and couples the leads to an extension. The surgeon then tunnels the extension down the neck of the patient, and couples the extension to the neurostimulator. The surgeon then incises the upper chest of the patient, implants the neurostimulator in a sub-clavicular pocket, and closes all of the incisions.

Implantation of an IMD at a remote site can be difficult and time-consuming from the perspective of a surgeon, particularly where the IMD is located a significant distance from the treatment or monitoring site. Moreover, the increased surgical time, increased surgical trauma, and increased amount of implanted material associated with the use of leads and extensions can increase the risk to the patient of complications associated with the implantation of the IMD.

SUMMARY

In general, the invention is directed to techniques for implantation of a low-profile IMD. In a one exemplary embodiment, the invention presents a method for implantation of a low-profile IMD locally under the scalp and on top of the skull or cranium of the patient. The method includes making an incision in the scalp of a head of a patient to create a scalp flap, creating a pocket between the scalp and the patient's skull, and placing at least a portion of a low-profile IMD in the pocket. The low-profile IMD may include a plurality of modules, covered in part by a flexible overmold.

The method may further include deployment of sensors, leads or other apparatus. For example, the method may include drilling one or more burr hole through the skull and inserting one or more leads through the burr hole. The method may further include anchoring the low-profile IMD to the skull.

In another embodiment, the invention is directed to a method that includes at least two surgical procedures. In a first surgical procedure, the method comprises making an incision in the scalp of a head of a patient to create a scalp flap, exposing a skull beneath the scalp flap, creating a pocket between the scalp and the skull and placing at least a portion of a dummy low-profile IMD in the pocket. The method also includes covering at least a portion of the dummy low-profile IMD with the scalp flap and suturing the scalp flap to close the incision. The dummy IMD lacks the functionality of a working IMD, but may serve to stretch the scalp of the patient, and may be used to provide information about the shape of the patient's skull. Information about the shape of the skull may be used to adjust the contours of the working IMD so that the working IMD is tailored to the skull. In the second surgical procedure, the method comprises removing the dummy low-profile IMD and implanting a working low-profile IMD in place of the dummy low-profile IMD.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
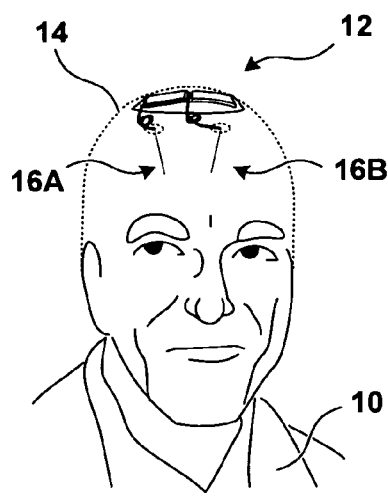
FIG. 1 is a conceptual diagram illustrating deployment of a low-profile IMD under the scalp of a patient.

FIG. 1 shows a patient 10 with a low-profile IMD 12 deployed beneath his scalp 14, according to an embodiment of the invention. In FIG. 1, IMD 12 is a neurostimulator that provides deep brain stimulation via leads 16A, 16B deployed in the brain of patient 10. As described in more detail below, IMD 12 is deployed in proximity to site of stimulation therapy. IMD 12 may be used to treat any nervous system disorder including, but not limited to, epilepsy, pain, psychological disorders including mood and anxiety disorders, movement disorders (MVD) such as, but not limited to, essential tremor and Parkinson's disease and neurodegenerative disorders.

Although IMD 12 is depicted as a neurostimulator, the invention is not limited to applications in which the IMD is a neurostimulator. The invention may be employed with low-profile IMDs that perform any monitoring or therapeutic functions. The invention is not limited to IMDs that include leads deployed in the brain, but may also be employed with leads deployed anywhere in the head or neck including, for example, leads deployed on or near the surface of the skull, leads deployed beneath the skull such as near or on the dura mater, leads placed adjacent cranial or other nerves in the neck or head, or leads placed directly on the surface of the brain. Nor is the invention limited to IMDs that are coupled to electrodes. The invention may be employed with low-profile IMDs coupled to any sensing or therapeutic elements, such as temperature sensors or motion sensors. The invention may also be employed with different types of IMDs including, but not limited to, IMDs operating in an open loop mode (also referred to as non-responsive operation), IMDs operating in a closed loop mode (also referred to as responsive), and IMDs for providing monitoring and/or warning.

Figure 2:
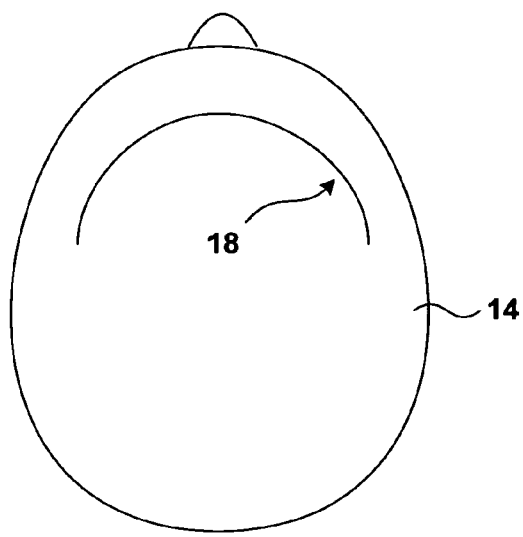
FIGS. 2-5 are plan diagrams of the top of a head of a patient, illustrating a procedure for implantation of a low-profile IMD.
Figure 3:
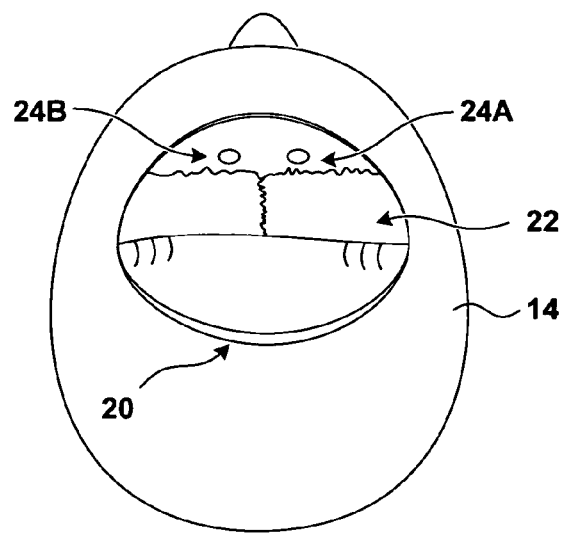

FIGS. 2-5 illustrate a procedure for implantation of low-profile IMD 12 shown in FIG. 1. FIG. 2 is a diagram showing the top of the head of patient 10. Patient 10 may be under local anesthetic. The surgeon begins implantation by making an incision such as C-flap incision 18 in scalp 14. In general, the surgeon has discretion concerning the making of an incision based upon the circumstances of each individual patient. Accordingly, the incision need not be a C-flap incision as shown in FIG. 2, but may include a straight incision or an S-shaped incision, for example. As shown in FIG. 3, the surgeon draws scalp flap 20 away to expose the portion of the patient's skull 22 that was beneath scalp flap 20. In the example in which patient 10 is to receive leads deployed in the brain, the surgeon may drill burr holes 24A and 24B for insertion of leads 16A and 16B into the brain. Typical burr holes are 14 mm in diameter.

Figure 4:
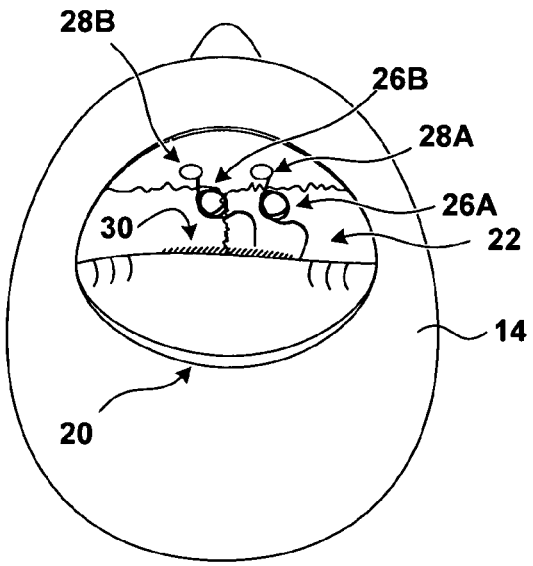
Figure 5:
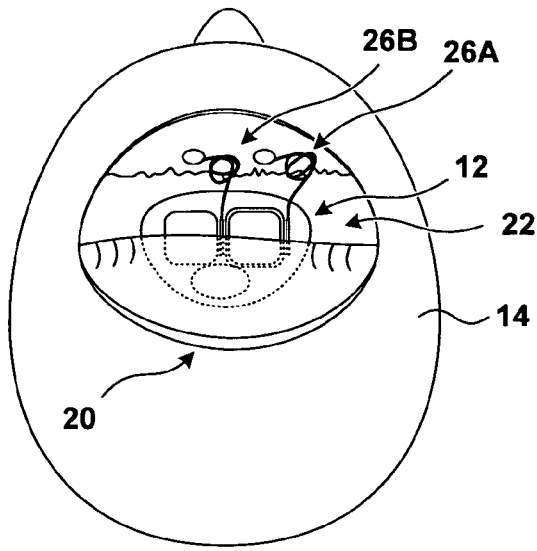

In FIG. 4, it is assumed that the surgeon has implanted leads 16A and 16B (not shown in FIG. 4) in the brain of patient 10. A portion of the leads, identified with reference numerals 26A and 26B, is deployed outside of the brain. The surgeon has also sealed the burr holes with caps 28A and 28B, with leads 26A and 26B passing therethrough. In addition, the surgeon has separated a part of scalp 14 from skull 22 at the fold of flap 20, creating a pocket 30. A flat spatula-like instrument may be used to create pocket 30. Pocket 30 may be an approximately semi-circular separation, and scalp 14 may be separated from skull 22. The pocket may be opened sufficiently to receive IMD 12 or a portion thereof. As shown in FIG. 5, the surgeon inserts low-profile IMD 12 into pocket 30, and couples IMD 12 to leads 26A and 26B. The surgeon may secure IMD 12 using any securing technique, such as by using bone screws. Leads 26A and 26B may be secured as described below. Flap 20 may be drawn over the portion of IMD 12 not inside pocket 30, and flap 20 may be sutured, thereby closing incision 18.

Figure 6:
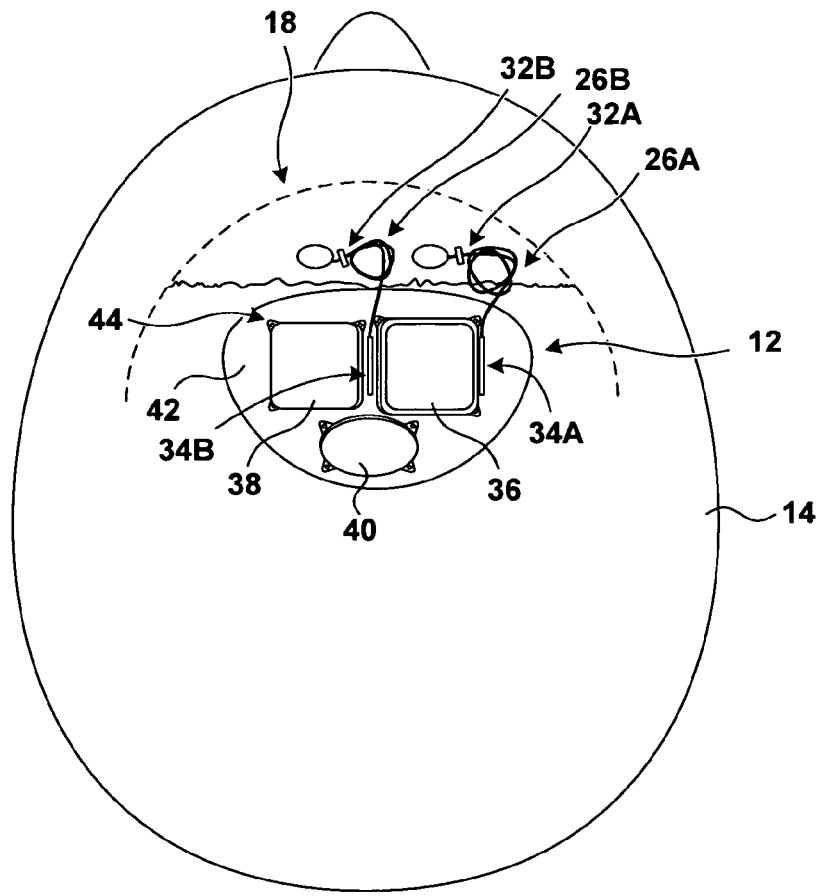
FIG. 6 is a plan diagram of the top of a head of a patient, illustrating deployment of one embodiment of a low-profile IMD.

FIG. 6 is a more detailed version of FIG. 5. In FIG. 6, scalp 14 is presumed to be transparent, and C-flap incision 18 is shown for reference. Leads 26A and 26B are anchored with anchoring plates 32A and 32B. Anchoring plates 32A and 32B, which may be made of titanium, secure leads 26A and 26B to skull 22. The anchoring sites shown in FIG. 6 are illustrative, and leads 26A and 26B may be anchored in other ways as well. The surgeon manages leads 26A and 26B by coiling leads 26A and 26B. Coiling is one technique for to managing excess lead length, and also provides some slack to reduce the risk of lead migration. Coiling also reduces the risk that leads 26A and 26B will be accidentally damaged if the incision is reopened at a later date. The invention is not limited to any particular technique of lead management. Additional details pertaining to lead connection modules and lead management are described in co-pending and commonly assigned U.S. patent applications entitled "LEAD CONNECTION MODULE OF A MODULAR IMPLANTABLE MEDICAL DEVICE," Ser. No. 10/730,878, and "OVERMOLD FOR A MODULAR IMPLANTABLE MEDICAL DEVICE," Ser. No. 10/730,873.

Leads 26A and 26B are coupled to IMD 12 at lead connectors 34A and 34B. As shown in FIG. 6, IMD 12 includes three modules, a control module 36, a power supply module 38 and a recharge module 40.

Control module 36 typically includes the electronic components associated with the functions of IMD 12. In a typical implementation, control module 36 may include a hybrid circuit that includes digital circuits such as integrated circuit chips and one or more microprocessors, and analog circuit components. Accordingly, control module 36 may also be referred to as an electronic module. Power supply module 38 typically comprises one or more energy storage devices, such as a rechargeable lithium ion battery. Recharge module 40 typically includes one or more coils for transmitting or receiving electromagnetic energy through scalp 14. The transmitted energy may include energy to be stored in power supply module 38. In some embodiments, the transmitted energy may also include communication, such as information encoded in radio frequency transmissions.

Individual modules 36 and 38 may be encased in biocompatible metal shields such as titanium shield halves, and may be sealed against contamination. In addition, individual modules 36 and 38 may include insulation to electrically isolate the electrical components inside the modules from the metal shields. The modules are coupled to an overmold 42 which may be made of a biocompatible material. Use of the term "overmold" herein is not intend to limit the invention to embodiments in which the overmold is a molded structure. Overmold may be a molded structure, or may be a structure formed by any process.

In some embodiments of the invention, overmold 42 encases all modules 36, 38, 40. In other embodiments, overmold 42 is disposed over or around the modules without encasing the modules. In further embodiments, overmold 42 acts as a "frame" to hold the modules in a fixed position relative to one another, but does not fully cover the modules. Some features of overmold 42, and variations on the shape of overmold 42, are presented below. In general, the shape of overmold 42 depends upon the arrangement of the modules. Overmold 42 may be made of a variety materials, such as flexible silicone. Overmold 42 may also include a rigid polymer such as Ticothane surrounded by flexible silicone.

As shown below, there are many possible module arrangements. The invention is not limited to the particular arrangements disclosed herein. In addition, the invention is not limited to any particular number of modules. Other embodiments may include more or fewer modules than are shown, and the modules may be arranged in countless different ways. Similarly, the arrangement of lead connectors 34A and 34B as shown in FIG. 6 is exemplary and the invention is not limited to any particular number of lead connectors or any particular placement of lead connectors. Also, IMD 12 typically includes interconnecting apparatus (not shown) that electrically couples the modules to one another. This interconnecting apparatus, which is typically flexible in one or more dimensions, may take a variety of configurations. Exemplary embodiments of modules 36, 38, 40, and exemplary embodiments of connectors and interconnecting members, may be described in one or more of the following co-pending and commonly-assigned U.S. patent applications, filed on even date herewith: U.S. patent application entitled "MODULAR IMPLANTABLE MEDICAL DEVICE," Ser. No. 10/731,869; U.S. patent application entitled "COUPLING MODULE OF A MODULAR IMPLANTABLE MEDICAL DEVICE," Ser. No. 10/731,699; U.S. patent application entitled "OVERMOLD FOR A MODULAR IMPLANTABLE MEDICAL DEVICE," Ser. No. 10/730,873; U.S. patent application entitled "REDUCING RELATIVE INTER-MODULE MOTION IN A DISTRIBUTED MODULAR IMPLANTABLE MEDICAL DEVICE," Ser. No. 10/731,881; U.S. patent application entitled "LEAD CONNECTION MODULE OF A MODULAR IMPLANTABLE MEDICAL DEVICE," Ser. No. 10/730,878; U.S. patent application entitled "LOW-PROFILE IMPLANTABLE MEDICAL DEVICE," Ser. No. 10/730,877; and U.S. patent application entitled "CONCAVITY OF AN IMPLANTABLE MEDICAL DEVICE," Ser. No. 10/731,867.

In a typical embodiment, each module in IMD 12 has a low profile, thereby giving IMD 12 as a whole a low profile. Exemplary embodiments of modules 36, 38, 40 may be, 5.8 mm thick or less. Overmold 42 need not add significant bulk on top of any module, and as a result, IMD may be about 6 mm thick at its thickest part. In one embodiment of the invention, the thickness of control module 36 is about 5 mm or less, the thickness of power supply module 38 is about 6 mm or less, and the thickness of recharge module 40 is about 3 mm or less. In this embodiment, IMD 12 exhibits a profile in which IMD 12 is about 6 mm thick at its thickest part, and is substantially thinner elsewhere.

The invention is not limited to devices having a maximum thickness of 6 mm, however. For some patients, a device with a maximum thickness of 8 mm could be deemed to be "low-profile," and for other patients, a device having a maximum thickness of 10 mm may be deemed to be "low-profile." In general, however, low-profile devices have a maximum thickness in the range of about 4 mm to 8 mm, with a thinner device generally being preferable to a thicker one. It is believed that some low-profile implantable devices may be thinner than 4 mm.

The thinness of the components gives IMD 12 a low profile. In addition, the modular construction of IMD 12 provides multiple degrees of freedom and flexibility. When inserted into pocket 30, IMD 12 can conform to the shape of the head of patient 10, and scalp 14 can be stretched to cover IMD 12. When the scalp incision is closed, IMD 12 creates a small bulge in scalp 14. Many patients can become accustomed to the presence of low-profile IMD 12 with less discomfort than would be caused by a bulkier implanted device. For many patients, the bulge is cosmetically manageable and therefore offers an advantage to the patients in terms of appearance and self-image. An additional advantage of the low profile of IMD 12 is that IMD 12 is less likely to be struck inadvertently and dislodged or damaged.

Reference number 44 indicates an exemplary anchoring mechanism to hold IMD 12 in place and prevent IMD 12 from migrating under scalp 14. In FIG. 6, anchoring mechanism 44 is a metallic tab with an opening for receiving a bone screw. A surgeon may drive a bone screw through overmold 42, through the opening in the tab and into skull 22. IMD 12, and the modules thereof, may include one or more anchoring mechanisms. The invention is not limited to the deployment of anchoring mechanisms as shown in the figures. Nor is the invention limited to anchoring mechanisms that include bone screws, but may encompass other anchoring mechanisms as well.

In FIG. 6, modules 36, 38 and 40 are arranged in a triangular configuration, with control module 36 and power supply module 38 being deployed anteriorly and recharge module 40 being deployed posteriorly. Overmold 42 is accordingly disposed in a rounded triangle shape around the perimeters of modules 36, 38 and 40. In a triangular configuration such as shown in FIG. 6, the average diameter of IMD 12 may be 10 cm or less.

Figure 7:
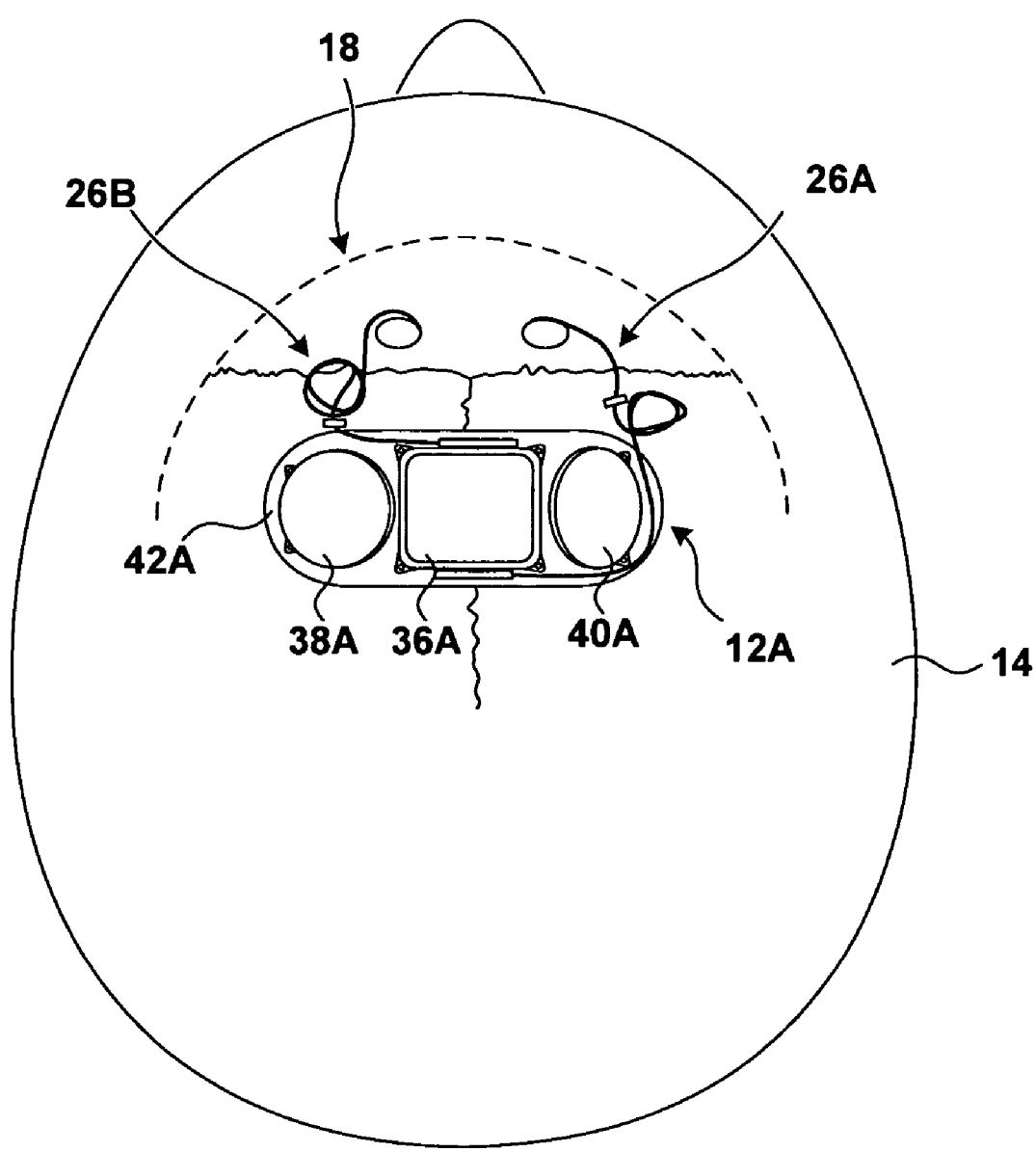
FIGS. 7-11 are plan diagrams of the top of a head of a patient, illustrating other exemplary embodiments of a low-profile IMD and exemplary deployments thereof.

In FIG. 7, by contrast, IMD 12A includes modules 36A, 38A and 40A arranged in a linear configuration. Overmold 42A is accordingly disposed in an elongated oval shape around the perimeters of modules 36A, 38A and 40A. IMD 12A is deployed with its long axis in the coronal direction.

The long axis typically would not exceed 15 cm. The procedure for implantation of IMD 12A is similar to the procedure for implantation of IMD 12. In particular, the surgeon makes an incision 18 in scalp 14, draws back scalp flap 20 and separates a part of scalp 14 from skull 22 to create a pocket. The surgeon inserts IMD 12A in the pocket.

IMD 12A includes some differences from IMD 12, which demonstrate the versatility of the invention. The techniques of the invention may be applied to different shapes of IMD, different arrangements of modules, different shapes of individual modules, different placements of leads and lead connectors, and so on.

Figure 8:
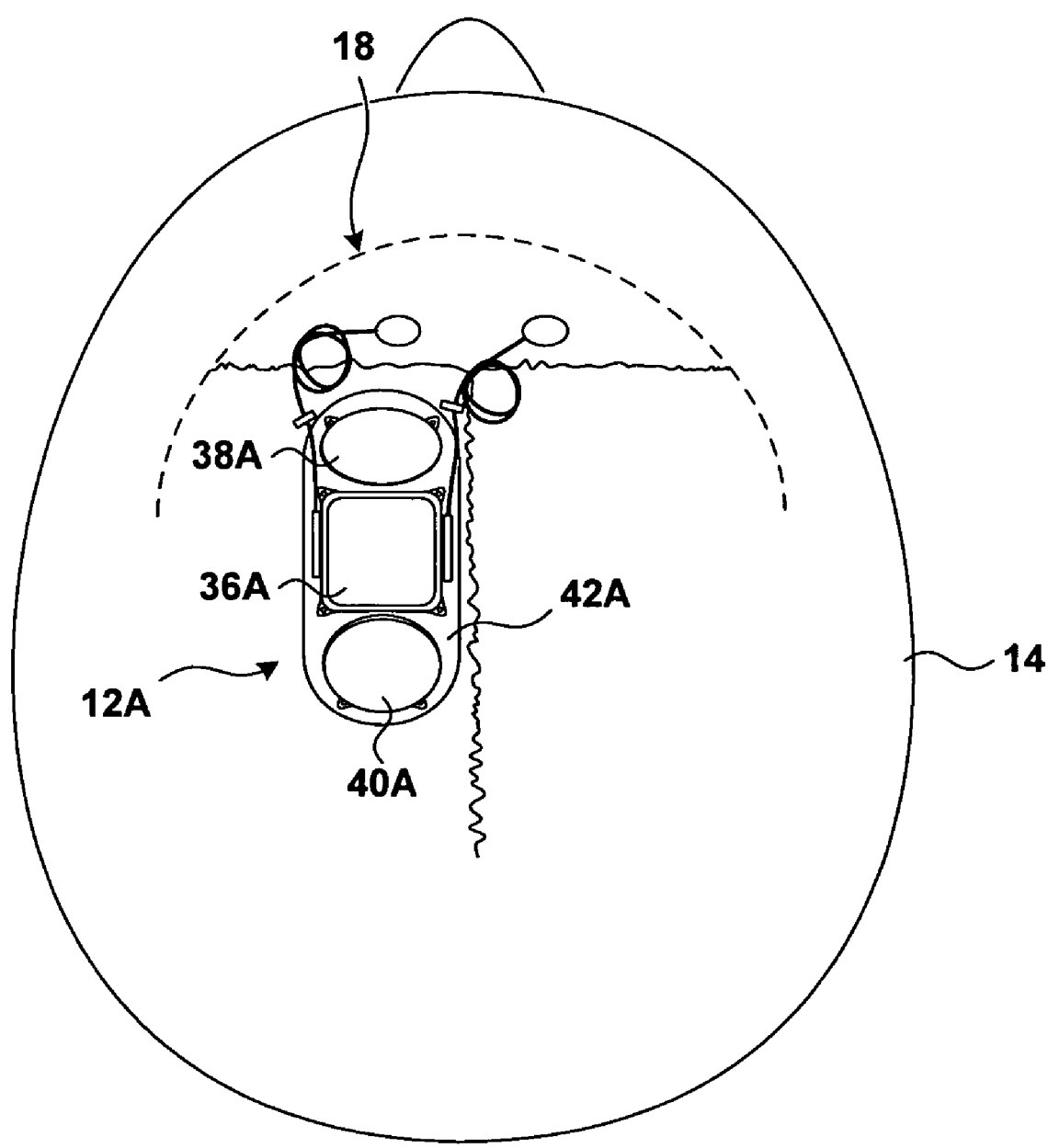

FIG. 8 depicts an alternate implantation orientation of IMD 12A. In FIG. 8, IMD 12A is deployed with its long axis substantially in the sagittal direction. Although FIG. 8 depicts IMD 12A as implanted offset from center, the invention also supports a midline implantation. The techniques of the invention may be applied to implant IMD at different sites and with a variety of orientations.

Figure 9:
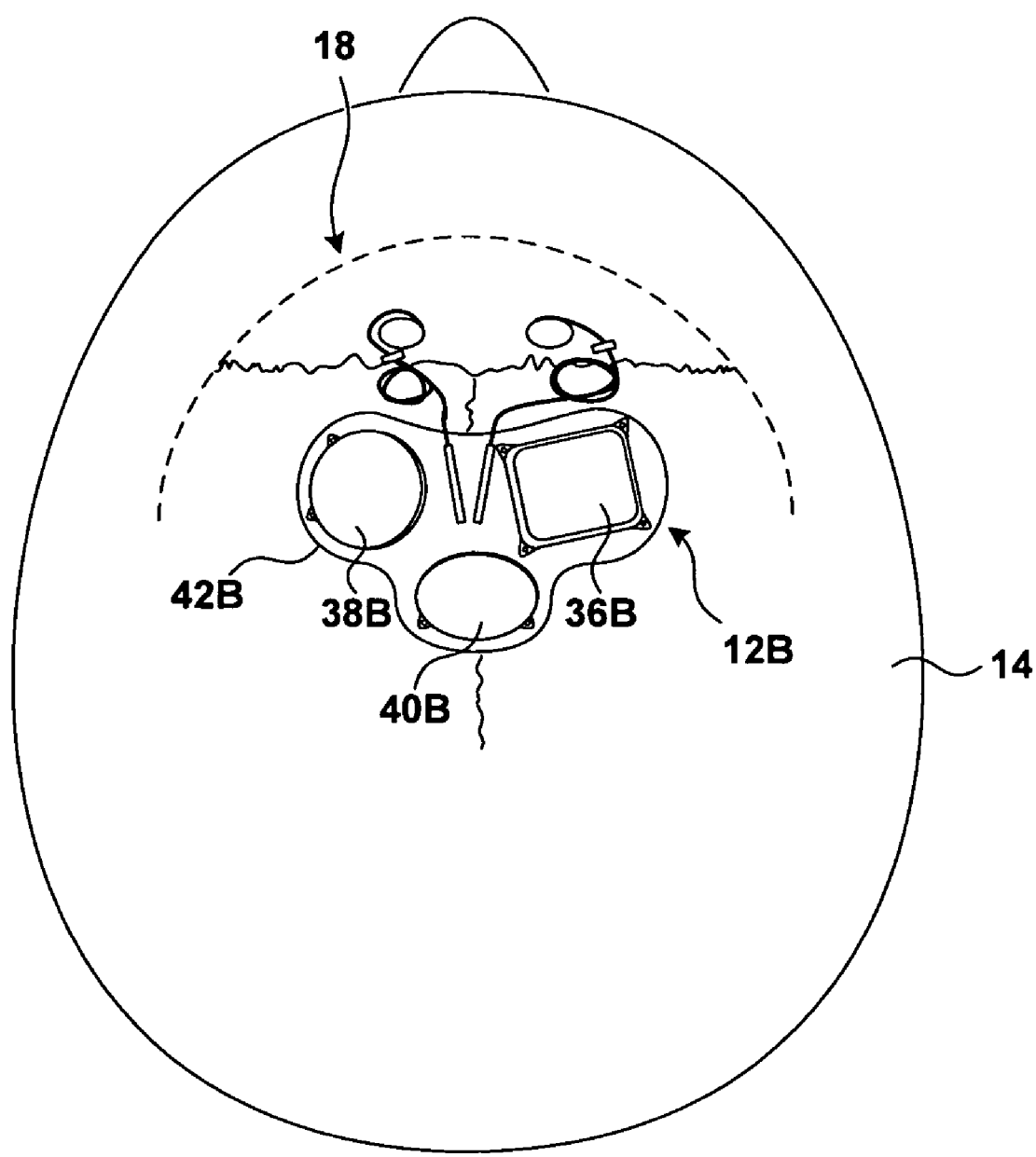

IMD 12B depicted in FIG. 9 includes modules 36B, 38B and 40B arranged in another triangular configuration. Unlike IMD 12 in FIG. 6, however, the modules in IMD 12B are more widely spaced. In addition, the shape of overmold 42B is trefoil-like with a perimeter that includes concave and convex portions. The shape of overmold 42 in FIG. 6, by contrast, is convex along its entire perimeter. The procedure for implantation of IMD 12B is similar to the procedure for implantation of IMD 12.

Figure 10:
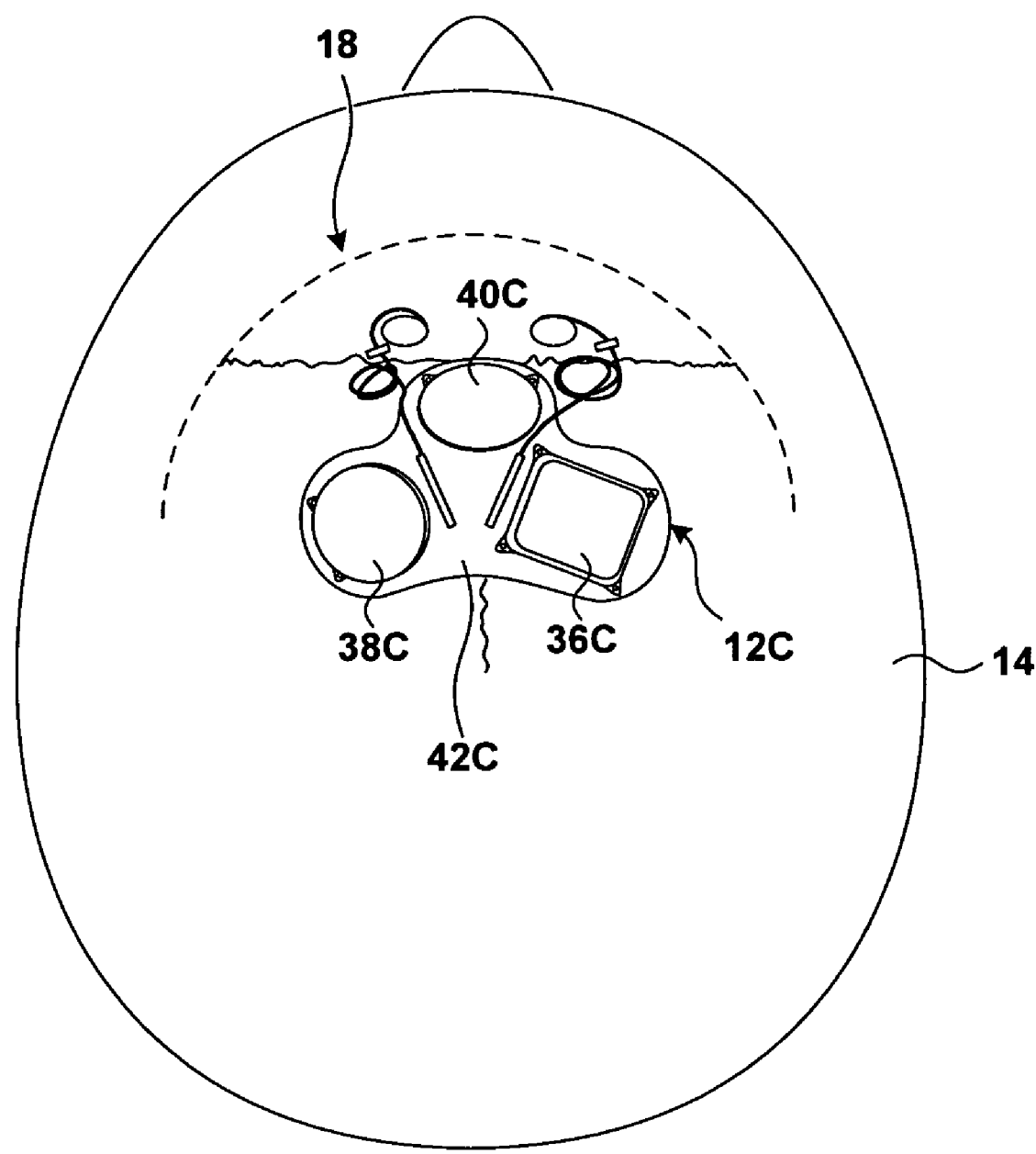

In FIG. 10, IMD 12C includes modules 36C, 38C and 40C arranged in a triangular configuration similar to that shown in FIG. 9, with a trefoil-like overmold 42C. Unlike IMD 12B, however, IMD 12C is configured to deploy recharge module 40C anteriorly and control module 36C and power supply module 38C posteriorly.

Figure 11:
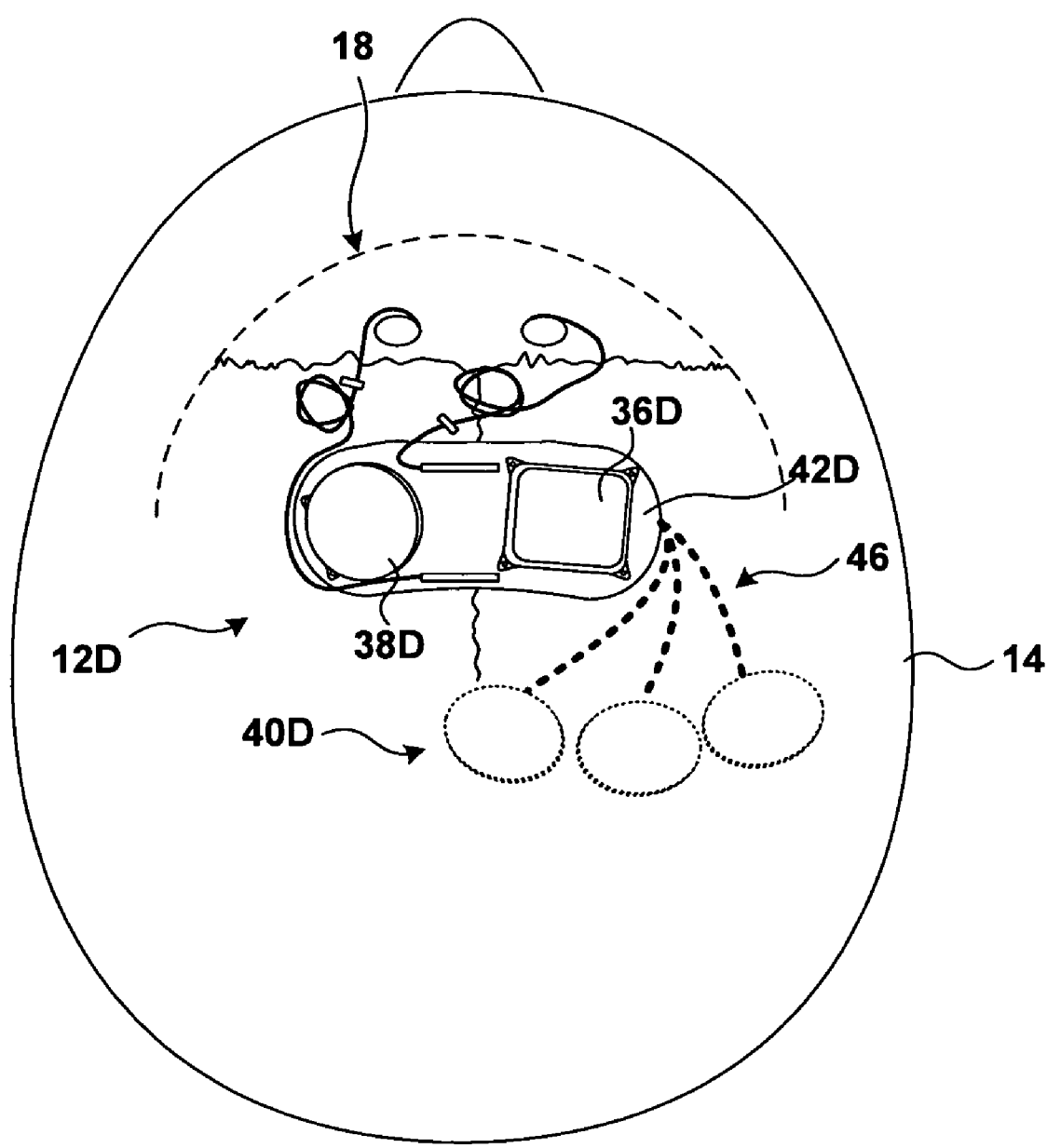

FIG. 11 depicts another arrangement of modules. IMD 12D includes control module 36D and power supply module 38D held by substantially oval overmold 42D. The long axis of IMD 12D is substantially along the coronal direction. Recharge coil 40D is not held by overmold 42D, but is movable with respect to other modules 36D, 38D, and is coupled to modules 36D, 38D with a flexible tether member 46. Flexible tether member 46 physically and electrically couples recharge coil 40D to one or more other components of IMD 12D.

During implantation of IMD 12D, the surgeon may prepare a pocket for control module 36D, power supply module 38D and overmold 42D, and a separate pocket for recharge coil 40D. In addition, the long axis of IMD 12D need not be oriented along the coronal direction as shown in FIG. 11.

Figure 12:
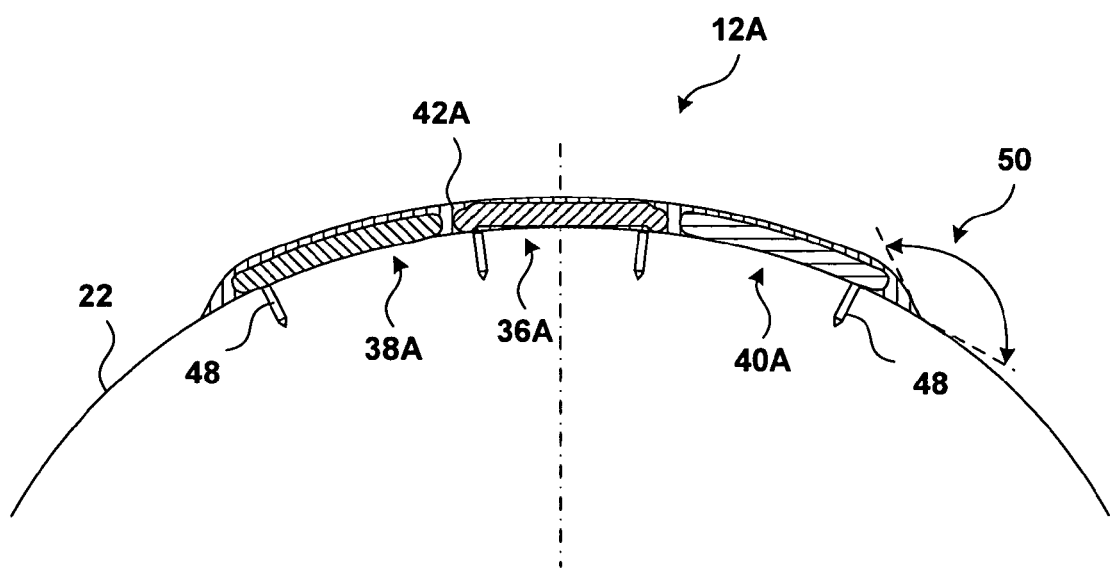
FIG. 12 is cross section of a skull and an illustrative embodiment of a low-profile IMD.

FIG. 12 depicts a cross-section of IMD 12A, which includes modules 36A, 38A and 40A arranged in a linear configuration, atop skull 22 of patient 10. IMD 12A follows the curvature of skull 22. In particular, overmold 42A flexibly adapts to the curvature of skull 22, allowing modules 36A, 38A and 40A to rest substantially flush on the surface of skull 22. In a typical implementation, overmold 42A is molded in a curved configuration prior to implantation, to accommodate a typical radius of curvature for an implantation site. A typical radius of curvature for the skull of an adult is about 7 cm across the top of the head. The typical radius of curvature may vary. For example, the radius of curvature for a typical adult skull becomes smaller as the skull slopes down to the temples. Accordingly, the curvature of overmold 42D may depend upon the size of the head of the patient and the expected implantation site.

In addition, modules 36A, 38A and 40A are each configured to substantially conform to the curvature of skull 22. Control module 36A, which may be substantially rigid, may include a central depression to accommodate some curvature of skull 22. Although power supply module 38A and recharge module 40A may be likewise substantially rigid, power supply module 38A is depicted in FIG. 12 as curved like a flask to accommodate some curvature of skull 22, and recharge module 40A is depicted in FIG. 12 as being flexible and capable of molding to the shape of skull 22.

In addition, the periphery of overmold 42A slopes down to the surface of skull 22 with a contoured edge. Angle 50, which represents the angle between the overmold periphery and a line tangent with skull 22, is typically greater than ninety degrees. In a typical application, angle 50 is about 135 degrees. When IMD 12A is implanted, angle 50 provides a gentle transition that softens the edges of the implanted device, making the device more comfortable and cosmetically manageable. The contoured edge of overmold 42A also reduces skin erosion. FIG. 12 shows IMD 12A anchored to skull 22 with one or more bone screws 48. Further description of adaptation of an IMD to a cranium is included in a co-pending and commonly-assigned U.S. patent application entitled "CONCAVITY OF AN IMPLANTABLE MEDICAL DEVICE," filed on even date herewith, and which is incorporated herein by reference in its entirety.

Figure 13:
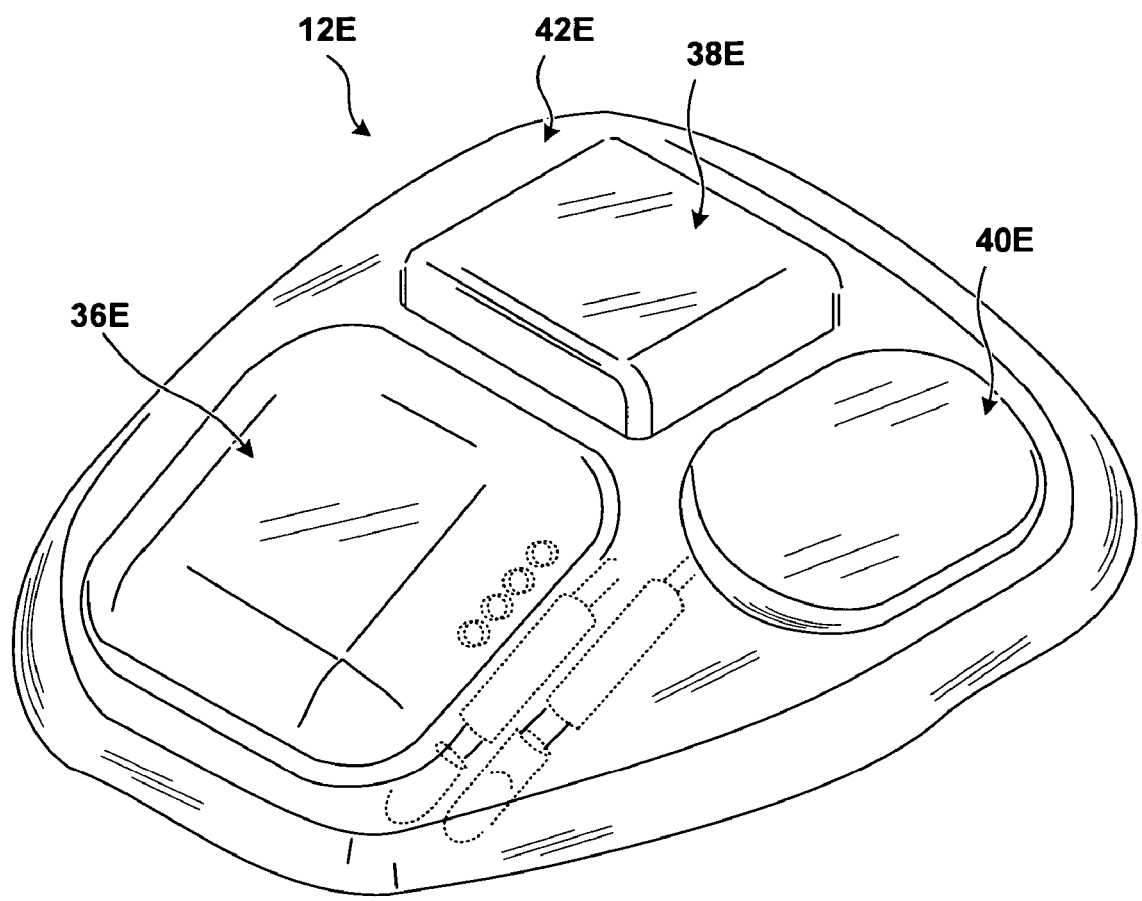
FIG. 13 is a perspective view of another embodiment of a low-profile IMD.

The embodiments of the IMD shown in FIGS. 6-11 may be adapted to fit a skull in a similar fashion. In other words, the modules and overmold may be arranged to fit the head of patient 10. Arrangement of modules and overmold to fit the head of a patient is illustrated in FIG. 13. FIG. 13 is a perspective view of an embodiment of IMD 12E in a triangular configuration. Even though IMD 12E is not implanted in a patient, IMD 12E as a whole is contoured in three dimensions to substantially conform to the shape of a skull. Overmold 42E helps retain the overall contours of IMD 12E, but also provides flexibility to IMD 12E. When applied to the skull of a patient, IMD 12E may conform to the shape of the skull without additional significant deformation.

The invention encompasses implantations of low-profile implantable medical devices that are adjustable during surgery. A surgeon may place a device proximate to the skull of a patient to determine whether the contour if the device matches the contour of the patient's cranium. If the device does not sit flush on the skull, the surgeon may make minor adjustments to the contour by bending, flexing or twisting the device, by hand or with a tool. By adjusting the device, the surgeon may cause the contour of the device to more closely match the contour of the patient's skull.

In some cases, implantation of an IMD may include an extra surgical stage. In particular, the surgeon may make a C-flap incision as shown in FIG. 2, and pull back the scalp flap to expose the skull. The surgeon may further separate a part of the scalp from the skull to create a pocket, as shown in FIG. 4, but the surgeon does not implant an IMD at that time. Instead, the surgeon implants a dummy IMD. The dummy may have approximately the same dimensions as a fully functional or "working" IMD, or may be larger or smaller than the working IMD. The dummy IMD may or may not include working components. After implantation of the dummy IMD, the surgeon sutures closed the scalp flap. No burr holes need be drilled or leads deployed during this procedure.

Although the dummy IMD need not provide sensing or therapy, the dummy IMD may serve several functions. First, the dummy IMD may help stretch or expand the scalp of the patient, thereby facilitating a later implantation of the working IMD. In one embodiment of the invention, the dummy IMD does not have a fixed volume, but may include a sac or pouch that can be expanded over time. The sac may comprise, for example, a self-sealing silicone envelope that can be increasingly filled by injection through the scalp with a fluid such as saline. With an expendable dummy IMD, the patient's scalp may stretch more gradually than with a fixed volume dummy IMD. Gradual stretching of the scalp with an expandable dummy IMD may effectively pre-condition a patient's scalp for the implantation of a working IMD, perhaps with less discomfort.

In addition, the dummy IMD may provide useful information about the actual shape or curvature of the head of the patient, allowing the contours of the working IMD to be adjusted as a function of the shape of the dummy IMD. For example, the dummy IMD may be more flexible than the working IMD, and the shape of the dummy IMD may be measured in vivo to assess the shape of the patient's skull. In another embodiment, the dummy IMD may include sensors that actively respond to the amount of deformation caused by implantation. Retrieval of information from the sensors likewise may convey information about the shape of the patient's skull. With data about the patient's skull, the working IMD can be tailored to the skull of the patient.

After a time, a second surgery may be performed to implant the working IMD and to deploy leads. At that time, the dummy IMD may be extracted.

In many cases, use of a dummy IMD may be unnecessary, and data collected via conventional imaging techniques may allow the IMD to be contoured substantially to the shape of the skull of the patient. Conventional imaging such as X-ray imaging may be employed prior to surgery to locate suitable implantation sites.

In addition, the surgeon may in some cases determine that the skull of the patient may be prepared to receive the IMD. The surgeon may, for example, create one or more troughs or recesses in the skull of the patient to receive the IMD or one or more modules thereof. Such recesses may give the IMD the external appearance of having a smaller profile. Some embodiments of the IMD, however, have such a low profile that it may not be necessary to create any recesses in the skull.

Although the invention has been described in connection with implantation on the head, the invention is not limited to implantation on the head. A low-profile IMD such as the devices described herein may be implanted anywhere in the body. Implantation techniques may be similar to techniques for implantation under the scalp. In particular, the surgeon may make an incision in the skin of a patient. The surgeon may retract the incision to expose a bone, muscle or other anatomical structure. The surgeon may create a pocket for the low-profile IMD proximate to the exposed anatomical structure. The surgeon may insert all or part of the IMD in the pocket and suture closed the incision.

The low-profile IMD is especially advantageous for head implantation, however, for many reasons. First, a low-profile IMD implanted on the skull can be proximate to treatment or monitoring sites on the head. Extensions may be unnecessary, as the leads may be coupled directly to the IMD. Further, tunneling through the patient's neck to a remote site for IMD implantation likewise becomes unnecessary, because the IMD can be implanted locally. As a result, implantation of an IMD can in many cases be preformed in a single surgical procedure, with less time needed for the surgery.

The invention supports implantation of an IMD at almost any site. The invention further supports implantation of a variety of IMDs, including IMDs that provide monitoring, IMDs that administer therapy, and IMDs that do both. The invention is not limited to any particular number of modules or to any particular functionality.

Various embodiments of the invention have been described. As mentioned above, the invention is not limited to the particular embodiments described or shown in the figures. These and other embodiments are within the scope of the following claims.

The invention claimed is:

1. A method comprising:
    making an incision in a scalp of a head of a patient to create a scalp flap;
    separating the scalp flap from a skull of the patient, wherein the separated scalp flap is attached to the remainder of the scalp by a fold;
    after separating the scalp flap from the skull, separating a portion of the remainder of the scalp adjacent to the fold from the skull to create a pocket adjacent to the fold and between the scalp and the skull;
    placing at least a portion of a low-profile implantable medical device in the pocket adjacent to the fold and underneath the scalp;
    drilling one or more burr holes in a portion of the skull of the patient exposed by separating the scalp flap from the skull; and
    inserting one or more leads through the burr holes and into a brain of the patient.

2. The method of claim 1, wherein the low-profile implantable medical device comprises:
    a first module that includes control electronics within a first housing;
    a second module that includes a second housing; and
    a flexible overmold that at least partially covers the first and second housings.

3. The method of claim 1, wherein the low-profile implantable medical device has a maximum thickness of between approximately 4 millimeters and approximately 8 millimeters.

4. The method of claim 1, wherein the low-profile implantable medical device has a maximum thickness of approximately 6 millimeters.

5. The method of claim 1, wherein the low-profile implantable medical device has a periphery and wherein the angle between the periphery and the skull, is greater than ninety degrees.

6. The method of claim 5, wherein the angle is approximately 135 degrees.

7. The method of claim 1, further comprising connecting the one or more leads to the low-profile implantable medical device.

8. The method of claim 1, further comprising anchoring the low-profile implantable medical device to the skull.

9. The method of claim 8, wherein anchoring the low-profile implantable medical device to the skull comprises anchoring the low-profile implantable medical device to the skull with a bone screw.

10. The method of claim 1, further comprising:
    covering an exposed portion of the low-profile implantable medical device with the scalp flap; and
    suturing the scalp flap to close the incision.

11. The method of claim 1, further comprising:
    creating a recess in the skull; and
    placing the low-profile implantable medical device in the recess.

12. The method of claim 1, further comprising:
    creating a second pocket between the scalp and the skull; and
    placing at least a portion of a low-profile implantable medical device in the second pocket.

13. The method of claim 12, wherein the low-profile implantable medical device comprises:
- a first module within a first housing;
- a flexible overmold that at least partially covers the first housings;
- a second module that includes a second housing; and
- a flexible tether member that couples the second module to the first module,
- wherein placing at least a portion of a low-profile implantable medical device in the second pocket comprises placing at least a portion of the second module in the second pocket.

14. The method of claim 1, wherein the low-profile implantable medical device is contoured in three dimensions to substantially conform to the shape of a skull.

15. The method of claim 1, further comprising adjusting the low-profile implantable medical device to cause a contour of the low-profile implantable medical device to more closely match a contour of the skull.

16. The method of claim 1, further comprising administering a local anesthetic to the patient prior to making the incision.

17. The method of claim 1, wherein the incision is made in a top of the head of the patient.

18. The method of claim 1, wherein placing at least a portion of the low-profile implantable medical device in the pocket comprises placing all of the low-profile implantable medical device in the pocket.

19. The method of claim 1, wherein the low-profile implantable medical device is a neurostimulator that provides deep brain stimulation.

20. The method of claim 1, wherein the incision is a C-flap incision.

21. A method comprising:
- making an incision in a scalp at a top of a head of a patient to create a scalp flap at the to of the head of the patient;
- separating the scalp flap from a skull of the patient, wherein the separated scalp flap is attached to the remainder of the scalp by a fold;
- after separating the scalp flap from the skull, separating a portion of the remainder of the scalp adjacent to the fold from the skull to create a pocket adjacent to the fold and between the scalp and the skull; placing at least a portion of a low-profile implantable medical device in the pocket adjacent to the fold and underneath the scalp;
- drilling one or more burr holes in a portion of the skull of the patient exposed by separating the scalp flap from the skull;
- inserting one or more leads through the burr holes and into a brain of the patient;
- connecting the one or more leads to the low-profile implantable medical device;
- covering the low-profile implantable medical device, leads and burr holes with the scalp flap; and
- closing the incision.

22. The method of claim 21, further comprising:
- creating a recess in the skull; and
- placing the low-profile implantable medical device within the recess.

23. A method comprising:
- making an incision in a scalp at a top of a head of a patient to create a scalp flap at the top of the head of the patient;
- separating the scalp flap from a skull of the patient, wherein the separated scalp flap is attached to the remainder of the scalp by a fold;
- after separating the scalp flap from the skull, separating a portion of the remainder of the scalp adjacent to the fold from the skull to create a pocket adjacent to the fold and between the scalp and the skull; and
- placing at least a portion of a low-profile implantable medical device in the pocket adjacent to the fold and underneath the scalp.

24. The method of claim 23, wherein placing the portion of the low-profile implantable medical device in the pocket adjacent to the fold and underneath the scalp comprises placing all of the low-profile implantable medical device in the pocket adjacent to the fold and underneath the scalp.

25. The method of claim 23, wherein the low-profile implantable medical device is a neurostimulator that provides deep brain stimulation.

* * * * *

UNITED STATES PATENT AND TRADEMARK OFFICE
CERTIFICATE OF CORRECTION

PATENT NO. : 8,397,732 B2
APPLICATION NO. : 10/731868
DATED : March 19, 2013
INVENTOR(S) : Singhal et al.

It is certified that error appears in the above-identified patent and that said Letters Patent is hereby corrected as shown below:

In the Claims:

Col. 11, Line 36: "at the to of the head" should read --at the top of the head--

Signed and Sealed this
Seventh Day of May, 2013

Teresa Stanek Rea
*Acting Director of the United States Patent and Trademark Office*